United States Patent
Whiteside

[11] Patent Number: 5,766,260
[45] Date of Patent: Jun. 16, 1998

[54] ACETABULAR COMPONENT WITH IMPROVED LINER SEAL AND LOCK

[76] Inventor: Leo A. Whiteside, 14825 Sugarwood Trail, Chesterfield, Mo. 63017

[21] Appl. No.: 847,887

[22] Filed: Apr. 28, 1997

Related U.S. Application Data

[63] Continuation of Ser. No. 466,607, Jun. 6, 1995, abandoned.

[51] Int. Cl.⁶ ............................................. A61F 2/34
[52] U.S. Cl. ............................................. 623/22
[58] Field of Search ........................... 623/18, 22, 23

[56] References Cited

U.S. PATENT DOCUMENTS

| | | | |
|---|---|---|---|
| 3,848,272 | 11/1974 | Nolles. | |
| 3,863,273 | 2/1975 | Averill. | |
| 4,044,403 | 8/1977 | D'Errico. | |
| 4,172,296 | 10/1979 | D'Errico. | |
| 4,380,090 | 4/1983 | Ramos. | |
| 4,619,658 | 10/1986 | Pappas et al.. | |
| 4,681,589 | 7/1987 | Tronzo | 623/22 |
| 4,904,265 | 2/1990 | MacCollum et al. | 623/22 |
| 4,936,861 | 6/1990 | Muller et al. | 623/22 |
| 5,021,062 | 6/1991 | Adrey et al. | 623/22 |
| 5,314,487 | 5/1994 | Schryver et al. | 623/22 |
| 5,443,519 | 8/1995 | Averill et al. | 623/22 |
| 5,480,448 | 1/1996 | Mikhail | 623/18 |

FOREIGN PATENT DOCUMENTS

| | | | |
|---|---|---|---|
| 0245527 | 11/1987 | European Pat. Off.. | |
| 2686791 | 8/1993 | France | 623/22 |

OTHER PUBLICATIONS

Multiple Defenses Against Poly Debris, Trilogy Acetabular System, 12 pages total.

The Precision Cementless Pathway by The Precision Osteolock Design Group, Jan., 1992 issue of *Howmedica Your Orthopaedic Resource*, pp. 1–8.Y

*Richards Modular Hip System*, Surgical Technique, Aug., 1992, 21 pages total.

The Furlong H–A.C. Thr advertisement, Joint Replacement Instrumentation Ltd., 1993, 1 page.

*Primary Examiner*—John G. Weiss
*Assistant Examiner*—Bruce E. Snow
*Attorney, Agent, or Firm*—Polster, Lieder, Woodruff & Lucchesi, L.C.

[57] ABSTRACT

An acetabular component for a hip replacement system comprises an acetabular shell, and a liner having a seal for insertion into the acetabular shell. In the preferred embodiment, the shell has a smooth tapered surface in its peripheral inner surface, and the liner has several annular ridges protruding from its outer surface. Upon insertion of the liner into the shell, the annular ridges of the liner come into sealing engagement with the smooth tapered surface of the shell. This sealing engagement substantially prevents a migration of debris along an interface of the liner with the shell. The liner is provided with several peripheral tabs for interference fit with several peripheral notches in the shell. An interlock comprising another liner ridge and a shell groove, provide a positive engagement to hold the liner in the shell as it bottoms therein. In an alternative embodiment, each notch is provided with protruding lips which project into the notch and firmly grasp one of the tabs of the liner upon insertion of the liner into the shell. In this manner, micromotion between the liner and the shell is substantially inhibited.

6 Claims, 1 Drawing Sheet

ACETABULAR COMPONENT WITH IMPROVED LINER SEAL AND LOCK

This application is a continuation of application Ser. No. 08/466,607 filed on Jun. 6, 1995 now abandoned.

BACKGROUND OF THE INVENTION

Prosthesis components for replacing anatomical joints are well known in the art, including total hip replacement systems. These systems include acetabular components and femoral components which interact with the acetabular components to replicate the articulation between the head of a femur and an acetabulum, or cotyloid cavity, of a pelvic girdle. The acetabular component typically comprises two parts, a metal acetabular shell and a polyethylene liner for insertion into the acetabular shell.

Acetabular shells typically have openings in the shell, including screw holes, which give rise to at least two problems. First, wear debris that is generated from the articular movement between a femoral head component and the liner can migrate between the liner and the acetabular shell, pass through the openings in the acetabular shell, and cause damage to the bone into which the acetabular shell is implanted. Second, debris can also be generated as a result of minor movement between the liner and the acetabular shell, commonly known as micromotion. This debris can also pass through the openings in the acetabular shell and cause damage to the bone.

Some efforts have been made to address this second problem, including providing an acetabular shell with a polished inner shell surface so as to minimize the amount of debris generated. Additionally, several manufacturers provide shells and liners with a variety of tongue and groove like configurations, such as generally rectangular tabs and indentations for mutual engagement. While these interlocking means serve to reduce the amount of debris generated by micromotion, they fail to solve the problem of migration of debris from the prosthetic articular surface between the acetabular shell and liner. Thus, despite these efforts, large numbers of polyethylene particles still have access to the acetabular bone.

Another approach, which attempts to address both of the debris problems mentioned above, particularly for acetabular shells having screw holes, is to utilize what are known as "man-hole covers," or plugs, for insertion into unused screw holes to prevent the migration of debris therethrough. The main disadvantage of this approach is that the plugs fail to prevent the migration of debris through holes that have bone screws inserted therethrough. The debris will still migrate around the screws and through the holes, and ultimately damage the bone. Additionally, many acetabular components are now made without screw holes to prevent migration of polyethylene debris into bone behind the metal shell, but this can compromise fixation of the shell to bone in cases in which screws are necessary.

The inventor herein is aware of only one design that obviates both of the problems mentioned above, but the usefulness of this design has its own limitations. The acetabular shell is provided with a tapered inner surface for interfacing with a liner having a corresponding taper. Because the taper interface must fit tightly with each other to be effective, it is virtually impossible to seat the polyethylene liner onto the inner dome surface of the metal shell. Because the liner only contacts the acetabular shell about the peripheral edge of the shell to create an annulus of contact, part of the liner, which extends into the acetabular shell, is unsupported. Although such a configuration does provide a sealing effect between the liner and the acetabular shell, the design is unsuitable as liners formed from polyethylene deform over time which interferes with the desired smooth motion between the head and liner. Moreover, because all the load exerted on the liner is concentrated at the peripheral interface with the acetabular shell, the thickness of the shell must be relatively large, which, for acetabular components of smaller joints, requires a relatively and unacceptably thin liner. If the tapered portions of the shell and liner are made large enough to avoid distortion of the polyethylene shell, then this leaves no room for screws to be placed through the most effective portion of the shell's dome.

What is needed is an acetabular component that provides a seal for the interface of the acetabular shell with the liner, that can substantially inhibit micromotion between the acetabular shell and liner, and that provides adequate support for the liner across substantially all of liner so that the liner can be formed from polyethylene.

SUMMARY OF THE INVENTION

The acetabular component for a hip replacement system according to the present invention comprises an acetabular shell and liner, with an integrally formed seal and interlock. The seal is formed between the acetabular shell and the liner upon insertion and interlock of the liner into the acetabular shell. The seal is provided to substantially prevent a migration of poly debris along an interface of the outer surface of the liner with an inner surface of the acetabular shell. The interlock provides a positive engagement between the liner and shell to indicate a complete and proper seating of the liner and shell. The outer surface of the liner is of a shape complementary to the inner surface of the acetabular shell so that substantially all of the outer surface of the liner is supported by the acetabular shell upon insertion of the liner into the shell.

In the preferred embodiment, the seal is provided as an integral part of the liner, and comprises several annular ridges protruding from the outer surface of the liner and having a generally sloped triangular cross-sectional configuration. The acetabular shell is provided with a peripheral, smooth portion in its inner surface and positioned so that the seal, or annular ridges, of the liner is in sealing engagement with the smooth inner surface upon insertion and interlock of the liner into the acetabular shell. The smooth portions could alternatively be rough or roughened with ripples or ridges, non-tapered, non-cylindrical, non-recessed, or otherwise shaped, oriented, or configured as long as they provide a sealing surface for the annular ridges. The interlock is also provided as an integral part of the liner and comprises an interrupted ridge extending circumferentially between the tabs, described infra. The shell has a matching interrupted groove extending between the notches, described infra. The interlock is engaged as the interrupted ridge moves into the groove and the liner seats within the shell.

The sealing engagement of the seal ridges with the smooth portion prevents debris generated by the articulation of a femoral head component with the inner surface of the liner from migrating along the liner/shell interface. This ultimately prohibits the debris from passing through openings in the acetabular shell and damaging the bone into which the acetabular component is implanted. Typically, these openings in the acetabular shell include screw holes provided for attaching the acetabular shell to the bone with bone screws.

All of the annular ridges and liner are formed from polyethylene, and are therefore resilient. During insertion of the liner into the acetabular shell, the seal ridges will flex as they are forced against the inner surface of the acetabular shell, and remain at least partially flexed as they are seated into the seal recess. As the interlock engages, the seal ridges will, due to their resiliency, attempt to return to their original configuration, and will then be in sealing engagement with the seal recess. Since the ridges are resilient, they allow the polyethylene liner to seat fully in the dome of the metal shell to achieve full support of the polyethylene.

The liner is provided with several peripheral tabs for interlocking engagement with several notches provided about the periphery of the acetabular shell. The tabs are rounded to facilitate insertion into the notches and are located to permit bottoming of the insert into the shell before they themselves bottom. In a first embodiment, the notch sidewalls are rectangular cut and form an opening slightly smaller than each tab to thereby provide an interference fit to control relative rotation. In an alternative embodiment, each notch has two lips projecting into the notch opening for firmly grasping a corresponding tab of the liner upon insertion of the liner into the shell. In either embodiment, the tabs of the liner must be forced into the notches of the shell, and in this manner, micromotion between the liner and the shell is substantially inhibited.

While the principal advantages and features of the invention have been described above, a greater understanding of the invention may be attained by referring to the drawings and the description of the preferred embodiment which follow.

DETAILED DESCRIPTION OF THE PREFERRED EMBODIMENT

Figure 1:
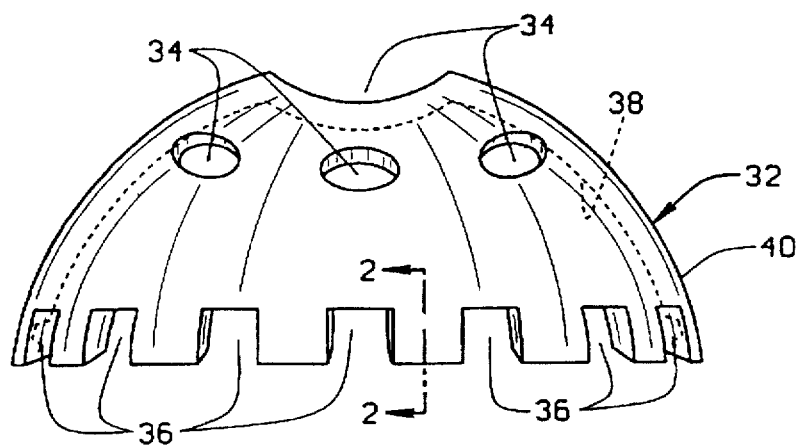
FIG. 1 is a perspective view of the shell of the acetabular component of the present invention.
Figure 2:
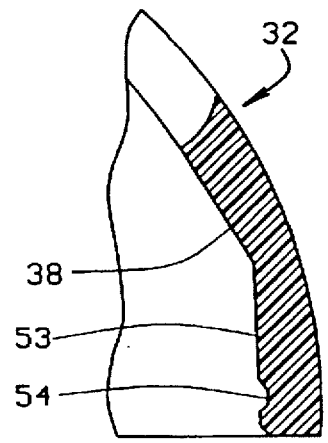
FIG. 2 is a cross-sectional view of the shell taken along the plane of line 2—2 in FIG. 1 and detailing the shell sealing surface and interlock groove.

The prosthesis component of the present invention is an acetabular component for a hip replacement system. FIG. 1 includes an acetabular shell 32 with a plurality of screw holes 34 and a plurality of peripheral notches 36. The acetabular shell 32 has an inner surface 38 and an outer surface 40. The outer surface 40 is generally hemispherical, and is contoured to closely match the shape of a hemispherically reamed acetabular, or cotyloid cavity, into which the shell 32 is to be implanted. The inner surface 38 of the shell 32 is also generally hemispherical, except near its peripheral edge which is relatively flat, and smooth as best seen in FIG. 2.

Figure 4:
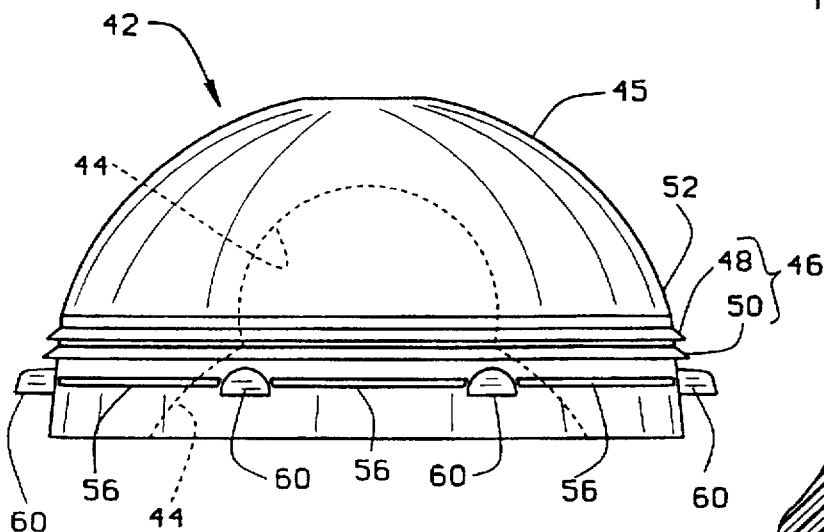
FIG. 4 is an elevational view of a liner of the acetabular component for insertion into an acetabular shell.
Figure 5:
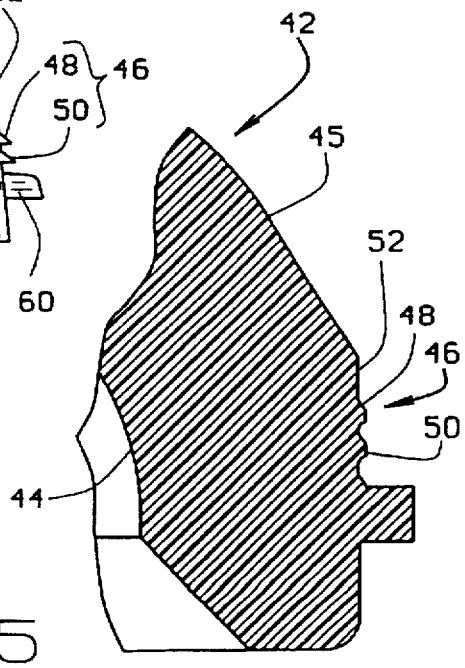
FIG. 5 is a partial view of the lower periphery of the liner and detailing the seal and interlock ridges.

The liner 42, as shown in FIGS. 4 and 5, is designed to be inserted into the acetabular shell 32. The liner has an inner surface 44 that interfaces with a femoral head component (not shown) of the hip replacement system. The liner is constructed from ultra high molecular weight polyethylene or other similar material, and has an outer surface 45 machined to a shape complementary to the inner surface 38 of the acetabular shell 32. As a result, substantially all of the hemispherical outer surface 45 of the liner is in mutual contact with the inner surface 38 of the acetabular shell 32 upon insertion of the liner 42 into the shell 32. This congruency between the liner and shell, while not necessary to realize the sealing aspects of the present invention, is structurally advantageous as it results in a distribution of forces from the femoral head component to be transmitted to the shell 32 through compression of liner 42, thereby allowing the shell 32 to be relatively thin.

As a result of articular movement between the femoral head component and the inner surface 44 of the liner 42, polyethylene and metal debris is generated. Ordinarily, this debris can migrate along the interface of the liner 42 and the shell 32, then through any opening in the shell 32, and consequently disease the bone. The congruency between the liner 42 and the shell 32, by itself, is insufficient to prevent this debris migration. For this reason, the liner 42 is provided with a peripheral seal 46 for substantially preventing a migration of debris. The seal 46 is positioned so that it forms a barrier for debris traveling between the shell inner surface 38 and the liner outer surface 45, towards the shell holes 34.

As shown in FIGS. 4 and 5, the seal 46 of the preferred embodiment is partially formed as an integral part of the liner 42. The seal 46 includes one or more annular ridges (two are shown) 48 and 50 which protrude from a peripheral, slightly-tapered surface 52 of the liner 42. Although two ridges 48, 50 are shown, it is contemplated that other numbers of ridges would also work effectively. As shown in FIG. 5, the annular ridges 48, 50 have a generally sloped configuration to ease insertion into the shell 32, although other configurations can be utilized with similar effect. With the sloped configuration shown, the ridges 48, 50 are readily flexed upon insertion of the liner 42 into the shell 32. The seal ridges 48, 50 are also formed from ultra high molecular weight polyethylene, and are therefore relatively resilient. Although the ridges 48, 50 have been described as being an integral part of the liner 42, the seal 46 could alternatively be provided as a separate component, or as an integral part of the shell 32. Additionally, other sealing configurations can also be used, and the seal 46 can be constructed from other suitable sealing materials as would be obvious to those skilled in the art.

Although the sealing surface of the shell is depicted smooth and tapered, it could also be rippled or have small ridges and still allow the flexible sealing ridge to achieve a tight seal. It could also be cylindrical with parallel walls and still allow sealing. The acetabular shell 32 of the preferred embodiment includes a matching slightly smooth tapered surface 53 formed along its peripheral inner surface which, as shown in FIG. 2, is positioned to receive the annular ridges 48, 50 with the ridges 48, 50 and the smooth tapered surface 53 in sealing engagement upon insertion of the liner 42 into the shell 32. The sealing engagement of the annular ridges 48, 50 with the annular sloped surface 53, upon insertion of the liner 42 into the acetabular shell 32, substantially prevents the migration of debris along the liner and shell interface.

In addition to the seal 46, the liner 42 "snap" fits and interlocks into shell 32 through an interlocking ridge and groove. As shown in FIG. 2, the smooth tapered surface 53 is "grooved" with an interlock groove 54 which receives an interrupted interlock ridge 56 which extends around the peripheral circumferential edge of liner 42. As liner 42 is inserted into shell 32 and "bottoms" out therein as desired, interlock ridge 56 "snaps" into interlock groove 54 to positively retain liner 42 within shell 32. This ensures that liner 42 mounts securely within and "bottoms" in shell 32 as desired, and also provides an indication to the surgeon that the liner 42 has been correctly and properly secured within shell 32. As with seal 46, the location of interlock groove 54 and interlock ridge 56 may be reversed, provided separately, or otherwise assembled with liner 42 and shell 32, and interlock ridge 56 need not be interrupted.

The shell screw holes 34 are utilized to secure the shell 32 to the acetabulum into which the shell 32 is implanted. Ordinarily, bone screws are inserted through one or more of screw holes 34 from inside the shell 32, and are then screwed into the bone contacting the outer surface 40 of the shell 32. Alternatively, modular pegs can be used instead of bone screws, or the shell 32 can be cemented or press fitted into an acetabulum, or some combination of these means for attaching. Although the shell 32 of the preferred embodiment is metallic, non-metallic materials could also be used in the construction of the shell.

While the shapes of the matching surfaces of the acetabular shell 32 and liner 42 have been described and shown as generally hemispherical, other shapes could be utilized in a particular application. As shown in the drawings, the surfaces are customarily machined to close tolerance to achieve an accurate conformance. It is desirable for the liner inner surface 44 to be generally hemispherical to accommodate rotational motion with a femoral component to simulate the articulation between a head of a femur and an acetabulum. Furthermore, while the acetabular component of the preferred embodiment utilizes only one seal 46 and one interlock, the acetabular shell can have more than one such seal, with each seal surface having one or more corresponding seal ridges 48 and 50 on the liner 42, without departing from the scope of the present invention. Alternately, the seal 46 could be located more closely to the screw holes 34, and even surround them separately or protrude into them.

In the preferred embodiment, the liner 42 is provided with one or more peripheral tabs 60 for engagement with several peripheral notches 36 in the shell 32 upon insertion of the liner 42 into the shell 32. For convenience in manufacture, peripheral notches 36 may be generally rectangular. The tabs 60 are sized to be slightly wider than each of notches 36 in order to provide an interference fit therebetween and thereby rotationally locate the liner 42 within shell 32. The upper surface of tabs 60 is generally sloped or rounded on either side to facilitate insertion of liner 42 and tabs 60 into shell 32 and notches 36, respectively. As explained above, as the liner outer surface 45 "bottoms" in the shell's inner surface 38, interlock ridge 56 engages interlock groove 54 which ensures that tabs 60 are sufficiently inserted into notches 36 so as to achieve an interference fit and reduce micromotion. As shown in FIGS. 1 and 4, in the preferred embodiment, six tabs 60 surround the circumference of liner 42 while twelve notches 36 surround the circumference of shell 32. The inventor has found that six tabs 60 are sufficient and adequate to securely position liner 42 within shell 32 while the additional notches 36 provide greater flexibility in alignment of the liner 42 with respect to the shell 32.

Figure 3:
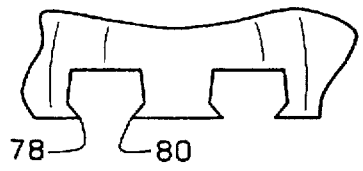
FIG. 3 is a partial view of an alternative embodiment of the shell notches.

To further prevent micromotion between the liner 42 and the shell 32, each notch 36 may be provided with protruding lips 78, 80 as shown in the alternative construction in FIG. 3. These lips 78, 80 project into the notches 36 and firmly grasp the tabs upon insertion of the liner 42 into the shell 32. In this manner, relative motion, or micromotion, between the liner 42 and the shell 32 is further substantially inhibited. Alternatively, the tabs 60 of the liner 42 could be lipped, and the notches 36 could have tapered sides, or the shell 32 could be provided with tabs 60 and the liner 42 provided with notches 36, with either the tabs 60 or the notches 36 being lipped, possibly in conjunction with tapered sides of the non-lipped member for ease of insertion.

While the liner 42 has been described as being formed from polyethylene, liners comprising other types of materials can also be used with the present invention where similar problems with debris generation or migration exist, or where sealing between the liner 42 and shell 32 is otherwise necessary.

To implant the acetabular components of the present invention, an appropriately sized component must be selected with consideration of anatomical and biomedical factors such as the patient's age, activity levels, weight, and bone and muscle conditions. Preparation of the acetabular cavity is necessary prior to insertion of the component. Thereafter, the acetabular shell can be inserted into the cavity and attached by any of the means described above. Where bone screws or modular pegs are to be utilized, the acetabular shell must be affixed prior to inserting the liner into the shell. Inserting the liner into the shell typically requires impacting the liner, which will cause the annular seal ridges to flex. The interlock ridge must also be forced past the outer lip of the shell and into the interlock groove which seats the liner in the shell, the seal, and the tabs into the notches. At that time, the annular seal ridges, due to their resiliency, will be in sealing engagement with the annular seal surface, thereby substantially preventing a migration of debris between the liner and shell. Meanwhile, the tabs of the liner have an interference fit into the notches, with the lips of each notch firmly grasping its respective tab (alternative embodiment), thereby substantially inhibiting micromotion between the liner and the shell.

While the prosthesis component of the present invention has been described as an acetabular component for a hip replacement system, this description is not intended to be limiting. The prosthesis component of the present invention can be utilized in other articulating anatomical joint systems, such as shoulder joint systems, and not limited to ball and socket joints, and is equally suited for other types of uses, including veterinarian applications.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. An acetabular component comprising:

an acetabular shell, said shell including at least one screw hole formed therein, said shell including a smooth inner sealing surface;

said acetabular shell also having at least one interlock circumferential groove and a plurality of peripheral notches formed therein;

a liner configured to seat within said acetabular shell, said liner including at least one circumferential peripheral annular seal, said at least one peripheral seal engaging said smooth inner sealing surface of said acetabular shell in a sealing engagement to restrict migration of debris toward said at least one screw hole;

said liner also including a separate raised locking ridge positioned to engage said interlock groove of said acetabular shell in a snap-lock arrangement; and a plurality of generally rounded peripheral tabs on the peripheral edge of said liner, said tabs disposed to engage said plurality of notches on said acetibular shell so as to prevent rotational movement of said liner within said acetabular shell.

2. The acetabular component of claim 1 wherein said acetabular component is load bearing, said liner being formed to substantially conform to and contact said shell under load bearing conditions, said at least one peripheral seal being positioned to maintain its sealing engagement between said liner and smooth inner sealing surface of said shell under load bearing conditions.

3. The acetabular component of claim 2 wherein said at least one seal includes at least one ridge of resilient material so that load bearing contact between said liner and said shell maintains said ridge a sealing engagement therebetween.

4. The acetabular component of claim 3 wherein each of said at least one ridges is an annulus integrally formed on said liner, and said smooth inner sealing surface is sized and spaced to receive and seat all of said at least one ridges, said seal thereby restricting migration of debris.

5. The acetabular component of claim 4 wherein said at least one seal extends annularly around the liner to thereby restrict debris from passing to the screw holes.

6. The acetabular component of claim 1 wherein each notch includes a pair of inwardly projecting lips to grasp said tabs as they engage.

* * * * *